United States Patent
Oguri et al.

(10) Patent No.: US 8,786,448 B2
(45) Date of Patent: Jul. 22, 2014

(54) STATE DETECTING DEVICE, STATE DETECTING METHOD, AND NON-TRANSITORY COMPUTER-READABLE MEDIUM

(75) Inventors: Koji Oguri, Handa (JP); Yoshifumi Kishimoto, Nagoya (JP)

(73) Assignee: Aisin Seiki Kabushiki Kaisha, Aichi-ken (JP)

( * ) Notice: Subject to any disclaimer, the term of this patent is extended or adjusted under 35 U.S.C. 154(b) by 166 days.

(21) Appl. No.: 13/383,085

(22) PCT Filed: Mar. 23, 2010

(86) PCT No.: PCT/JP2010/055010
§ 371 (c)(1),
(2), (4) Date: Jan. 9, 2012

(87) PCT Pub. No.: WO2011/004641
PCT Pub. Date: Jan. 13, 2011

(65) Prior Publication Data
US 2012/0105234 A1 May 3, 2012

(30) Foreign Application Priority Data
Jul. 9, 2009 (JP) .................................. 2009-163143

(51) Int. Cl.
*G08B 23/00* (2006.01)
(52) U.S. Cl.
USPC ....................... 340/576; 340/825.19; 340/5.52
(58) Field of Classification Search
USPC ......... 340/576, 501, 506, 540, 603, 657, 575, 340/573.1, 825.19, 5.52, 5.82
See application file for complete search history.

(56) References Cited

U.S. PATENT DOCUMENTS

| | | | |
|---|---|---|---|
| 5,416,861 A * | 5/1995 | Koh et al. | 385/14 |
| 2002/0091473 A1 | 7/2002 | Gardner et al. | |
| 2002/0116156 A1 | 8/2002 | Remboski et al. | |
| 2002/0120371 A1 | 8/2002 | Leivian et al. | |
| 2002/0120374 A1 | 8/2002 | Douros et al. | |

(Continued)

FOREIGN PATENT DOCUMENTS

| CN | 1862227 A | 11/2006 |
|---|---|---|
| CN | 1870939 A | 11/2006 |

(Continued)

OTHER PUBLICATIONS

International Search Report of PCT/JP2010/055010 dated Apr. 20, 2010.

(Continued)

*Primary Examiner* — Daniel Previl
(74) *Attorney, Agent, or Firm* — Sughrue Mion, PLLC

(57) ABSTRACT

Disclosed is a state detecting device that detects characteristic quantities regarding the driver that are represented by biological information such as the eyelid opening degree and frequency of heartbeat of the driver, identifies the group to which the state of the driver belongs between a Group 1 and a Group 2 into which multiple classes defined using the activity level of the driver as an indicator are sorted based on the detected characteristic quantities, outputs information including the identification results as output values, and detects the class to which the current state of the driver belongs based on loss values calculated from the output values. From the detected class, to what degree the activity level of the driver is impaired can be detected along with the level.

11 Claims, 7 Drawing Sheets

(56) References Cited

U.S. PATENT DOCUMENTS

| | | |
|---|---|---|
| 2002/0151297 A1 | 10/2002 | Remboski et al. |
| 2005/0128092 A1* | 6/2005 | Bukman et al. ............... 340/576 |
| 2007/0078351 A1 | 4/2007 | Fujita et al. |
| 2009/0011907 A1* | 1/2009 | Radow et al. .................... 482/57 |
| 2009/0097701 A1* | 4/2009 | Nagai et al. ................... 382/100 |
| 2012/0002843 A1 | 1/2012 | Yoda et al. |
| 2012/0209457 A1* | 8/2012 | Bushnell ......................... 701/13 |

FOREIGN PATENT DOCUMENTS

| | | |
|---|---|---|
| CN | 101002685 A | 7/2007 |
| CN | 101032405 A | 9/2007 |
| CN | 101281646 A | 10/2008 |
| CN | 101375796 A | 3/2009 |
| JP | 2005-158077 A | 6/2005 |
| JP | 2007-233475 A | 9/2007 |
| JP | 2007-265377 A | 10/2007 |
| JP | 2008-217274 A | 9/2008 |
| JP | 2008-243031 A | 10/2008 |
| JP | 2008-250859 A | 10/2008 |
| JP | 2008-282022 A | 11/2008 |
| JP | 2009-090028 A | 4/2009 |

OTHER PUBLICATIONS

Masahiro Miyaji, et al., "Detection of Driver's Cognitive Distraction by Means of Using AdaBoost with Physiological Signals", Journal of Information Processing Society of Japan, Jan. 2009, pp. 171-180, vol. 50, No. 1.

Japanese Office Action, dated Apr. 9, 2013, issued in corresponding Japanese Patent Application No. 2009-163143.

Chinese Search Report, dated Aug. 8, 2013, issued in corresponding Chinese Patent Application No. 2010800310258.

* cited by examiner

FIG.5

$$W = \begin{pmatrix} & \text{CLASS 1} & \text{CLASS 2} & \text{CLASS 3} & \text{CLASS 4} \\ & 1 & -1 & -1 & -1 \\ & -1 & 1 & -1 & -1 \\ & -1 & -1 & 1 & -1 \\ & -1 & -1 & -1 & 1 \\ & 1 & 1 & -1 & -1 \\ & 1 & -1 & 1 & -1 \\ & 1 & -1 & -1 & 1 \\ & 0 & 1 & -1 & -1 \\ & 0 & -1 & 1 & -1 \\ & 0 & -1 & -1 & 1 \\ & 1 & 0 & -1 & -1 \\ & -1 & 0 & 1 & -1 \\ & -1 & 0 & -1 & 1 \\ & 1 & -1 & 0 & -1 \\ & -1 & 1 & 0 & -1 \\ & -1 & -1 & 0 & 1 \\ & 1 & -1 & -1 & 0 \\ & -1 & 1 & -1 & 0 \\ & -1 & -1 & 1 & 0 \\ & 1 & -1 & 0 & 0 \\ & 1 & 0 & -1 & 0 \\ & 1 & 0 & 0 & -1 \\ & 0 & 1 & -1 & 0 \\ & 0 & 1 & 0 & -1 \\ & 0 & 0 & 1 & -1 \end{pmatrix}$$

STATE DETECTING DEVICE, STATE DETECTING METHOD, AND NON-TRANSITORY COMPUTER-READABLE MEDIUM

CROSS REFERENCE TO RELATED APPLICATIONS

This application is a National Stage of International Application No. PCT/JP2010/055010 filed Mar. 23, 2010, claiming priority based on Japanese Patent Application No. 2009-163143, filed Jul. 9, 2009, the contents of all of which are incorporated herein by reference in their entirety.

TECHNICAL FIELD

The present invention relates to a state detecting device, state detecting method, and non-transitory computer-readable medium.

BACKGROUND ART

State detecting devices for assessing the activity level of drivers are disclosed, for example, in Patent Documents 1 and 2 and a Non-Patent Document 1.

The state detecting device disclosed in the Patent Document 1 calculates the standard deviation of the movement of the vehicle in the direction perpendicular to the travelling direction. This state detecting device detects the vigilance level of the driver based on the results of comparing the calculated maximum and minimum standard deviations with thresholds.

The state detecting device disclosed in the Patent Document 2 continuously detects the direction of sight line of the driver for a given period of time. This state detecting device creates sight line profile information presenting the profile of the detected sight line direction. The state detecting device determines whether the driver is driving inattentively based on the direction of sight line presented by the created sight line profile information.

The state detecting device disclosed in the Non-Patent Document 1 detects the heart rate of the driver fluctuating according to his/her mental stress as a characteristic quantity. This state detecting device detects the driving stress of the driver by matching of the characteristic quantity using Ada-Boost.

PRIOR ART DOCUMENTS

Patent Documents

Patent Document 1: Unexamined Japanese Patent Application KOKAI Publication No. 2008-250859;
Patent Document 2: Unexamined Japanese Patent Application KOKAI Publication No. 2008-243031; and

Non-Patent Documents

Non-Patent Document 1: Information Processing Society of Japan Journal Vol. 50, No. pp. 171-180 (2009).

DISCLOSURE OF INVENTION

Problems to be Solved by the Invention

Different drivers have different driving habits and exhibit different behavioral patterns depending on their vigilance level. However, the state detecting devices disclosed in the Patent Documents 1 and 2 detect the state of a driver in a fixed manner. Therefore, the state detecting devices disclosed in the Patent Documents 1 and 2 are incapable of detecting the state of an individual driver with accuracy.

On the other hand, the state detecting device disclosed in the Non-Patent Document 1 detects the state of an individual driver based on the results of learning the driving habit of the driver. However, the state detecting device disclosed in the Non-Patent Document 1 simply classifies the state of a driver into a normal driving state and a non-normal driving state. Therefore, the state detecting device disclosed in the Non-Patent Document 1 is incapable of detecting the driver's stress in a non-normal driving state.

The present invention is invented under the above circumstances and an exemplary object of the present invention is to detect the state of an individual monitored subject by the level.

Means for Solving the Problem

In order to achieve the above object, the state detecting device of the present invention comprises a characteristic quantity detector for detecting information regarding a monitored subject as characteristic quantities; an identification device for receiving the characteristic quantities as input values, identifying a group to which a state of the monitored subject belongs between a first group and a second group into which multiple classes defined using the activity level of the monitored subject as an indicator are sorted based on the characteristic quantities, and outputting information including the identification results as output values; a loss value calculator for calculating loss values from the output values output from the identification device; and a class detector for detecting the class to which the state of the monitored subject belongs based on the loss values.

Furthermore, the multiple classes may be sorted into the first group and second group in multiple patterns.

Furthermore, the loss value calculator may define the loss values using an exponential function.

Furthermore, provided that the number of the classes is p and the number of the identification device is G, each of the identification device may output a sign indicating that the activity level of the monitored subject belongs to the first group consisting of the classes corresponding to the elements of a value "1" in each row of a code table W presented by $W \in \{1, 0, -1\}^{p \cdot G}$ or to the second group consisting of the classes corresponding to the elements of a value "−1" and an absolute value indicating the credibility.

Furthermore, the loss value calculator may obtain the loss defined by an exponential function for each of the identification device and each of the classes based on the sign and credibility output from the identification device and the code table W, and further obtain the sum of losses corresponding to the same class.

The class detector may detect the class of which the sum of losses is the smallest as the class to which the state of the monitored subject belongs.

Furthermore, the information regarding the monitored subject may be biological information of the monitored subject.

Furthermore, the biological information of the monitored subject may include information on the sight line of the monitored subject.

Furthermore, the biological information of the monitored subject may include information on the heartbeat of the monitored subject.

The characteristic quantity detector supplies the detected characteristic quantities to the identification device.

In order to achieve the above object, the state detecting method of the present invention includes an identification process to receive characteristic quantities that are indicators of a state of a monitored subject as input values, identify a group to which the state of the monitored subject belongs between a first group and a second group into which multiple classes defined using the activity level of the monitored subject as an indicator are sorted based on the characteristic quantities, and output information including the identification results as output values; a loss value calculation process to calculate loss values from the output values output in the identification process; and a class detection process to detect the class to which the state of the monitored subject belongs based on the loss values.

In order to achieve the above object, the non-transitory computer-readable medium stored a program of the present invention allows a computer to execute an identification step of receiving characteristic quantities that are indicators of a state of a monitored subject as input values, identifying a group to which the state of the monitored subject belongs between a first group and a second group into which multiple classes defined using the activity level of the monitored subject as an indicator are sorted based on the characteristic quantities, and outputting information including the identification results as output values; a loss value calculation step of calculating loss values from the output values output in the identification step; and a class detection step of detecting the class to which the state of the monitored subject belongs based on the loss values.

Effect of the Invention

The present invention allows for detecting the state of an individual monitored subject by the level.

BRIEF DESCRIPTION OF DRAWINGS

[FIG. 5] An illustration showing an example of the code table when the number of classes G is 4;

BEST MODE FOR CARRYING OUT THE INVENTION

<Embodiment 1>

A state detecting device 10 according to Embodiment 1 of the present invention will be described hereafter with reference to FIGS. 1 to 4. The state detecting device 10 according to this embodiment acquires biological information of a driver driving a vehicle. The state detecting device 10 detects the driving state of an individual driver based on the acquired biological information along with the level thereof.

Figure 1:
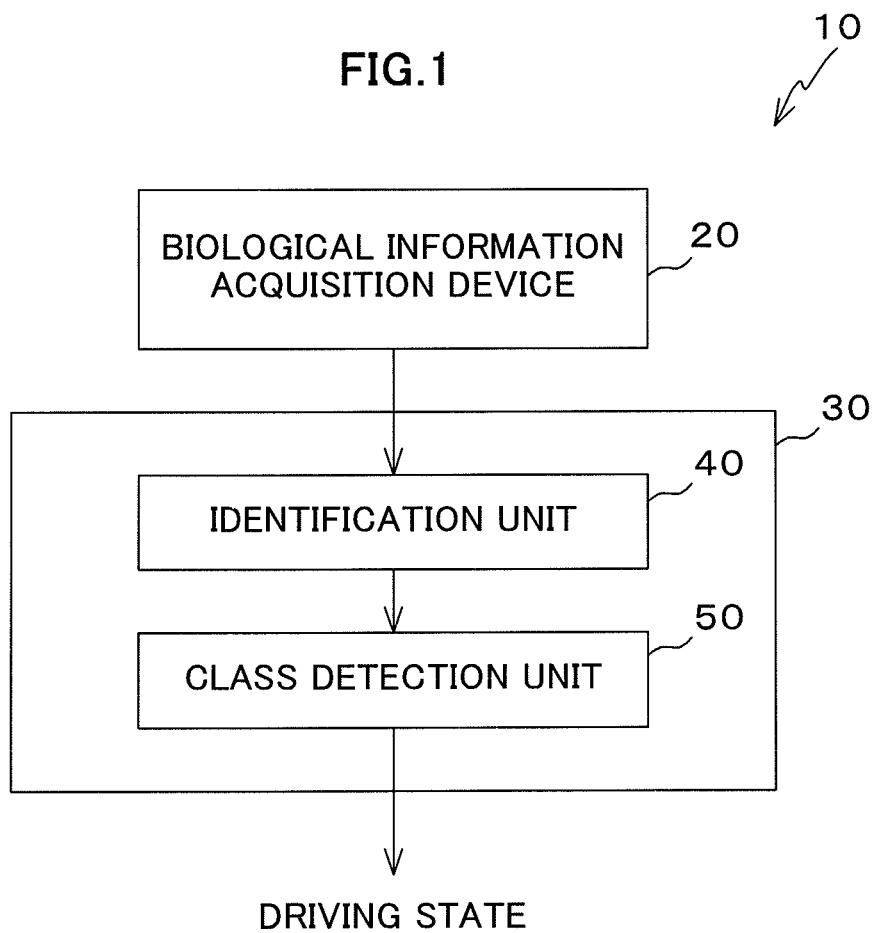
[FIG. 1] A block diagram of the state detecting device according to Embodiment 1.

The state detecting device 10 comprises, as shown in FIG. 1, a biological information acquisition device 20 acquiring biological information of a driver and detecting characteristic quantities thereof, and an identification device 30 detecting the driving state of the driver based on the characteristic quantities detected by the biological information acquisition device 20 along with the level thereof.

The biological information acquisition device 20 acquires, for example, information regarding the degree of opening of the eyelid due to drowsiness and information regarding the frequency of heartbeat as biological information of the driver.

The biological information acquisition device 20 acquires the eyelid opening degree information by analyzing eyelid images. Using the acquired eyelid opening degree information, the biological information acquisition device 20 detects the driver's eyelid opening degree normalized in a range from 0 to 1 as a characteristic quantity $a1$. Furthermore, the biological information acquisition device 20 acquires the frequency of heartbeat information by analyzing the RR intervals. Using the acquired frequency of heartbeat information, the biological information acquisition device 20 detects the frequency of the heartbeat interval variability of the driver in a low frequency range as a characteristic quantity $a2$ and the same in a high frequency range as a characteristic quantity $a3$ based on the heart rate fluctuation power spectral. The biological information acquisition device 20 outputs information $x$ ($a1$, $a2$, $a3$) regarding the detected characteristic quantities to the identification device 30. Here, the information $x$ ($a1$, $a2$, $a3$) regarding the detected characteristic quantities is simply referred to as the input information $x$ hereafter.

The identification device 30 detects the class to which the driving state of the driver belongs among, for example, three classes (Class 1, Class 2, and Class 3) defined using the activity level of the driver as an indicator. The identification device 30 has an identification unit 40 and a class detection unit 50.

The activity level of a driver can be defined by the length of time to take an action (reaction time) in the event that the driver takes an action in response to external input. The reaction time of a driver tends to be increased due to drowsiness or impaired attentiveness. For example, the reaction time of a driver is measured under various circumstances. The state of the driver when he/she needs a short reaction time is assumed to be the normal state and referred to as Class 1. On the other hand, the state of the driver when he/she needs a long reaction time (the most inattentive state) is referred to as Class 3. Furthermore, the state between the Classes 1 and 3 (an inattentive state) is referred to as Class 2. In this way, the state of a driver is classified into three classes.

Figure 2:
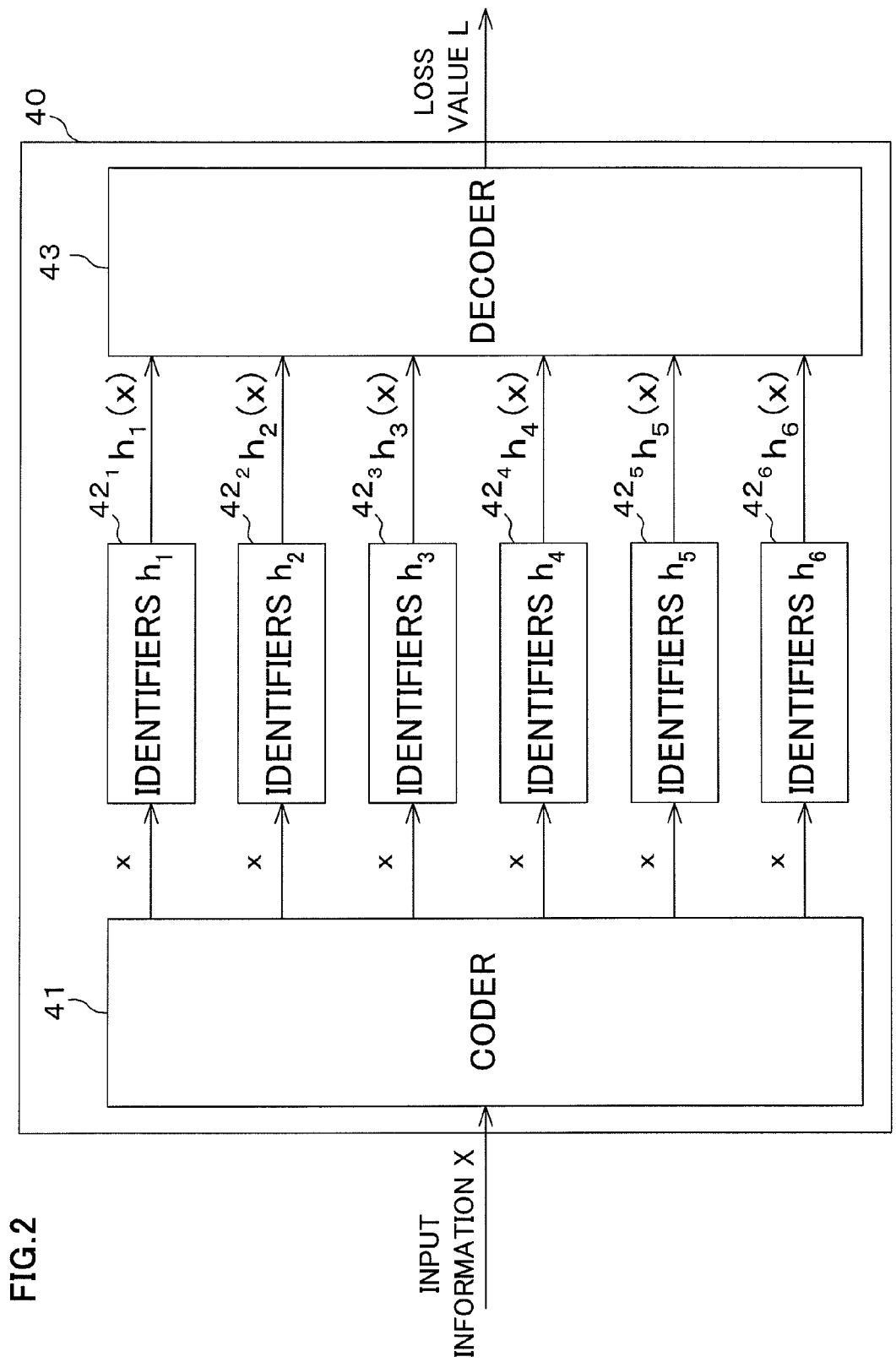
[FIG. 2] A block diagram of the identification unit.

The identification unit 40 comprises, as shown in FIG. 2, a coder 41, six identifiers 42₁ to 42₆, and a decoder 43.

The coder 41 executes a coding process using a code table W presented by the formula (1) below. Here, p is the number of identifiers and G is the number of classes. Each row of the code table W includes both "1" and "−1." In this embodiment, the number of classes to which the driving state belongs is 3 and the number of identifiers is 6. Therefore, the code table W presented by the general formula (1) below consists of 18 elements arranged in a matrix of 6 rows and 3 columns as presented by the formula (2) below.

[Formula 1]

$$W \in \{1, 0, -1\}^{p \times G} \quad (1)$$

[Formula 2]

$$W = \begin{pmatrix} 1 & -1 & -1 \\ -1 & 1 & -1 \\ -1 & -1 & 1 \\ 1 & -1 & 0 \\ 1 & 0 & -1 \\ 0 & 1 & -1 \end{pmatrix} \quad (2)$$

Figure 3:
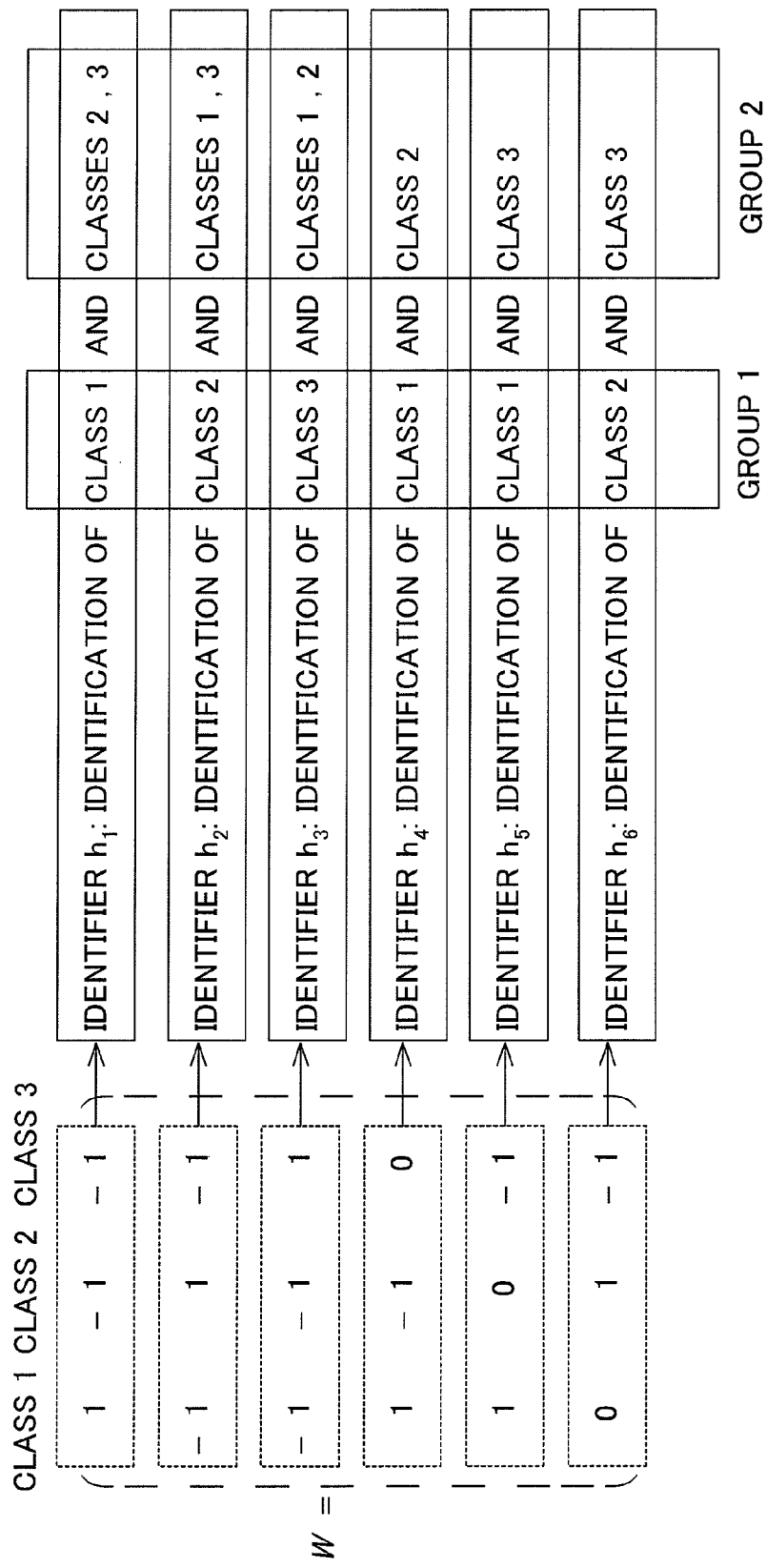
[FIG. 3] An illustration for explaining the operation of the identifiers.

As shown in FIG. 3, the three elements in each row of the code table W correspond to Class 1, Class 2, and Class 3, respectively, from the left to right. The three classes are sorted into a Group 1 consisting of the classes corresponding to the elements of a value "1" and a Group 2 consisting of the classes corresponding to the elements of a value "−1." Here, each group may consist of one class or multiple (two) classes. Furthermore, the classes corresponding to the elements of a value "0" are excluded from the sorting (they are sorted into neither of the Group 1 and the Group 2). For example, as for the three elements in the row 1 of the code table W, the Class 1 is sorted into the Group 1 and the Classes 2 and 3 are sorted into the Group 2.

Similarly, as for the three elements in the row 2 of the code table W, the Class 2 is sorted into the Group 1 and the Classes 1 and 3 are sorted into the Group 2. Furthermore, as for the three elements in the row 3 of the code table W, the Class 3 is sorted into the Group 1 and the Classes 1 and 2 are sorted into the Group 2. As for the three elements in the row 4 of the code table W, the Class 1 is sorted into the Group 1 and the Class 2 is sorted into the Group 2. As for the fifth elements in the row 5 of the code table W, the Class 1 is sorted into the Group 1 and the Class 3 is sorted into the Group 2. As for the three elements in the row 6 of the code table W, the Class 2 is sorted into the Group 1 and the Class 3 is sorted into the Group 2.

Receiving the input information x, the coder 41 outputs a code i consisting of the three elements in a row i (i=1 to 6) of the code table W and the input information x to an identifier 42$i$.

More specifically, receiving the input information x, the coder 41 associates a code 1 [1, −1, −1] consisting of the three elements in the row 1 of the code table W with the input information x. The coder 41 outputs the input information x associated with the code 1 to an identifier $42_1$.

Similarly, the coder 41 associates a code 2 [−1, 1, −1], a code 3 [−1, −1, 1], a code 4 [1, −1, 0], a code 5 [1, 0, −1], and a code 6 [0, 1, −1] each consisting of the three elements in the corresponding rows 2 to 6 of the code table W with the input information x, respectively. The coder 41 outputs the input information x associated with the corresponding codes 2 to 6 to the identifiers $42_2$ to $42_6$ corresponding to the codes 2 to 6, respectively.

The identifiers $42_1$ to $42_6$ are binary discriminators having the same structure and having undergone an AdaBoost learning process. Receiving the input information x, the identifier 42$i$ sorts multiple classes into the Group 1 or the Group 2 based on the code supplied to it. Then, the identifier 42$i$ identifies (determines) the state (activity state) of the driver presented by the input information x (a1, a2, a3) as belonging to the Group 1 consisting of the classes to which the element "1" of the code i is assigned or as belonging to the Group 2 consisting of the classes to which the element "−1" of the code i is assigned, and outputs the identification result and a credibility level indicating the accuracy of the identification result to the decoder 43.

For example, the code 1 [1, −1, −1] is supplied to the identifier $42_1$. Therefore, the identifier $42_1$ identifies "the state of the driver" presented by the input information x (a1, a2, a3) as belonging to the Group 1 consisting of the Class 1 (normal state) to which the element "1" is assigned or as belonging to the Group 2 consisting of the Class 2 (an inattentive state) and Class 3 (the most inattentive state) to which the element "−1" is assigned. Then, the identifier $42_1$ outputs an output value $h_1$ (x) indicating the identification result and a credibility (likelihood) level thereof.

The output value $h_1$ (x) consists of a numeric value with a sign (±). The sign of the output value $h_1$ (x) corresponds to the sign of the elements forming the code. When the sign of the output value $h_1$ (x) is +(>0), the identifier $42_1$ has identified the driving state of the driver presented by the input information x as belonging to the Group 1 (Class 1). On the other hand, when the sign of the output value $h_1$ (x) is −(<0), the identifier $42_1$ has identified the driving state of the driver presented by the input information x as belonging to the Group 2 (Class 2 or Class 3). Furthermore, the absolute value of the output value $h_1$ (x) indicates the credibility level of the identification result identified by the identifier $42_1$.

For example, when the identifier $42_1$ identifies the state of the driver presented by the input information x as belonging to the Group 2 (Class2 or Class 3) and determines that the credibility level thereof is |2|, the identifier $42_1$ outputs "−2" as $h_1$ (x).

Similarly, the identifiers $42_2$ to $42_6$ each identify "the state of the driver" presented by the input information x as being sorted into the Group 1 consisting of the classes to which the element "1" is assigned or as being sorted into the Group 2 consisting of the classes to which the element "−1" is assigned. Then, the identifiers $42_2$ to $42_6$ output $h_2$ (x) to $h_6$ (x) corresponding to the identification results, respectively.

For example, when the identifier $42_2$ identifies the state of the driver presented by the input information x as belonging to the Group 2 (Class 1 or Class 3) and determines that the credibility level is |7|, the identifier $42_2$ outputs "−7" as $h_2$ (x). Similarly, when the identifier $42_3$ identifies the state of the driver as belonging to the Group 1 (Class 3) and determines that the credibility level is |0.5|, the identifier $42_3$ outputs "0.5" as $h_3$ (x). When the identifier $42_4$ identifies the state of the driver as belonging to the Group 2 (Class 2) and determines that the credibility level is |1|, the identifier $42_4$ outputs "−1" as $h_4$ (x). When the identifier $42_5$ identifies the state of the driver as belonging to the Group 2 (Class 3) and determines that the credibility level is |9|, the identifier $42_5$ outputs "−9" as $h_5$ (x). When the identifier $42_6$ identifies the state of the driver as belonging to the Group 1 (Class 2) and determines that the credibility level is |12|, the identifier $42_6$ outputs "12" as $h_6$ (x).

The decoder 43 executes a decoding process using the code table W presented by the formula (2) above. As described above, the six elements in the column 1 of the code table W indicate which group the Class 1 is sorted into, the Group 1 or the Group 2. Furthermore, the six elements in the column 2 of the code table W indicate which group the Class 2 is sorted into, the Group 1 or the Group 2. Furthermore, the six elements in the column 3 of the code table W indicate which group the Class 3 is sorted into, the Group 1 or the Group 2.

The output values from the identifiers $42_1$ to $42_6$ represent an Euclidean distance from the identification plane and are equivalent to the credibility level of the identification result. Therefore, provided that the Group 1 is defined by the elements of a value "1" and the Group 2 is defined by the elements of a value "−1," the driving state of the driver is more liable to belong to the Group 1 as the output values $h_n$ (x) from the identifiers $42_1$ to $42_6$ are positive-signed and higher in value. On the other hand, the driving state of the driver is more liable to belong to the Group 2 as the output values $h_n$ (x) from the identifiers $42_1$ to $42_6$ are negative-signed and lower in value (higher in absolute value).

Then, the decoder 43 calculates loss values $L_1$ to $L_3$ corresponding to the Classes 1 to 3, respectively, using the output values from the identifiers $42_1$ to $42_6$ and the elements in the column direction of the code table W. The loss values $L_1$ to $L_3$ are calculated by the function presented by the formula (3) below.

[Formula 3]

$$L_k = \sum_{j=1}^{p} \begin{cases} \exp(|h_j(x)|) & \text{if } W_{jk} \cdot h_j(x) < 0 \\ -\exp(|h_j(x)|) & \text{if } W_{jk} \cdot h_j(x) > 0 \\ 0 & \text{if } W_{jk} \cdot h_j(x) = 0 \end{cases} \quad (3)$$

$$= \sum_{j=1}^{p} \{-\text{sign}(W_{jk} \cdot h_j(x)) \cdot \exp(|h_j(x)|)\}$$

Figure 4:
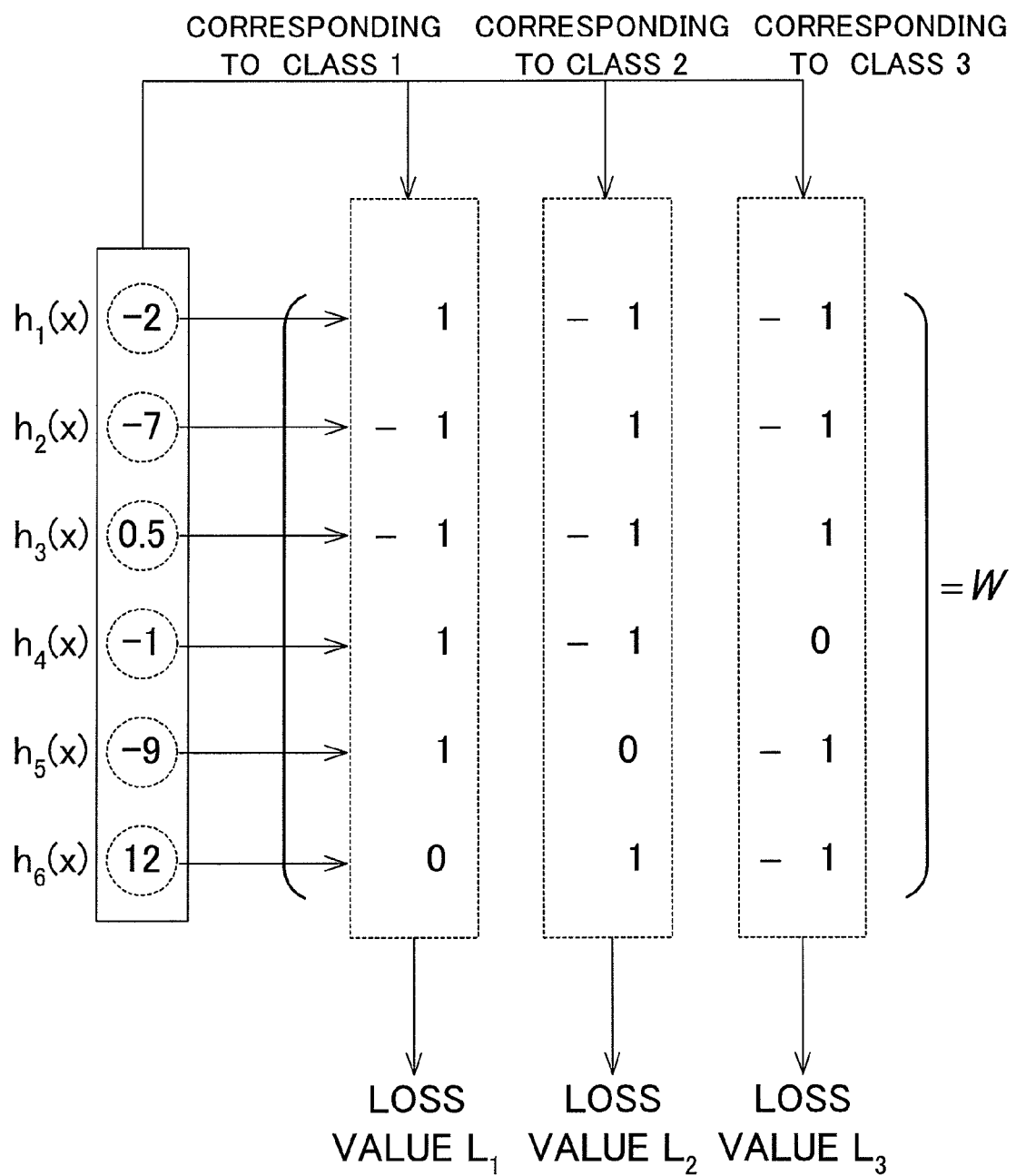
[FIG. 4] An illustration for explaining the method of calculating the loss values.

According to the above-described example, it is assumed that the output values $h_1$ (x) to $h_6$ (x) are −2, −7, 0.5, −1, −9, and 12 as shown in FIG. 4. In such a case, the loss value $L_1$ corresponding to the Class 1 is calculated as presented by the formula (4) below.

[Formula 4]

$$L_1 = \exp(2) - \exp(7) + \exp(0.5) + \exp(1) + \exp(9) - 0 \quad (4)$$
$$= 7018$$

The decoder 43 similarly calculates the loss values $L_2$ and $L_3$ corresponding to the Classes 2 and 3, respectively. Here, the loss value $L_2$ is −161667 and the loss value $L_3$ is 163546. The decoder 43 outputs the calculated loss values $L_1$ to $L_3$ to the class detection unit 50.

Returning to FIG. 1, the class detection unit 50 detects the class corresponding to the lowest loss value among the loss values $L_1$ to $L_3$ output from the decoder 43. The class detection unit 50 outputs the detected class to an external device as the class to which the driving state of the driver belongs. For example, when the loss values $L_1$ to $L_3$ output from the decoder 43 are 7018, −161667, and 153546, respectively, as described above, the class detection unit 50 outputs the Class 2 corresponding to the lowest loss value $L_2$ to an external device as the class to which the driving state of the driver belongs.

As described above, the state detecting device 10 according to this Embodiment 1 detects the class to which the current driving state of the driver belongs based on the driver's characteristic quantities represented by biological information such as the eyelid opening degree and frequency of heartbeat of the driver. The class is one of multiple classes defined by classifying the driving state of the driver using the activity level of the driver as an indicator. Therefore, to what degree the activity level of the driver is impaired can be detected by the level based on the detected class regardless of difference between individuals or difference in an individual. Consequently, driving assist more proper to the driver can be provided.

The tendency and variation of the above characteristic quantities vary depending on the driving state of the driver. Therefore, the biological information of the driver is not restricted to the above-described eyelid opening degree and frequency of heartbeat. For example, it is possible to further acquire multiple pieces of biological information such as blood pressure and body temperature and take such biological information into consideration to detect the class to which the driving state belongs, whereby the driving state of the driver can be detected more accurately and sorted into a larger number of levels.

Furthermore, in this Embodiment 1, the identifiers $42_1$ to $42_6$ are binary discriminators having undergone an Adaboost learning process. However, the present invention is not confined thereto and the identifiers $42_1$ to $42_6$ can be, for example, binary discriminators such as SVMs (support vector machines).

This embodiment utilizes the ECOC (error correcting output coding) method that is a method of extending a binary discriminator to the multivalued.

In another example, the three classes can be as follows: Class 1 is the normal driving state (a state of the driver being capable of normal driving), Class 2 is a state of the driver being absorbed in thought or absent-minded among non-normal driving states (drowsy or inattentive driving, driving in fatigue, hasty driving, stress, distracted, etc.), and Class 3 is a state of the driver talking with somebody among the non-normal driving states.

Furthermore, the number of classes, p, is not limited to 3. For example, the driving state of the driver can be classified into four or more classes using the activity level of the driver as an indicator. For example, when there are four classes, the code table W as shown in FIG. 5 is used.

Using the activity level of the driver as an indicator, the driving state of the driver can be classified into, for example, five classes corresponding to fully alert, slightly drowsy, drowsy, fairly drowsy, and severely drowsy states in conformity to the definition by the New Energy and Industrial Technology Development Organization (NEDO).

Assuming that the number of classes is G, the size $W_{size}$ (the number of rows) of the code table W can be obtained by the formula below. The number of columns is equal to the number of classes G.

[Formula 5]

$$W_{SIZE} = (3^G - 2^{G+1} + 1)/2 \quad (5)$$

Furthermore, when the number of identifiers, p, and the number of classes, G, are fixed, the code table W is fixed. In such a case, it is possible to omit the coder and allow the identifiers to conduct binary determination assigned to them in advance. In the above example, the identification device 30 is configured as follows. The coder 41 is omitted and the input information x is directly supplied to the identifiers $42_1$ to $42_6$. The identifier $42_1$ identifies "the state of the driver" presented by the input information x as belonging to the Group 1 consisting of the Class 1 or as belonging to the Group 2 consisting of the Classes 2 and 3; the identifier $42_2$ identifies "the state of the driver" as belonging to the Group 1 consisting of the Class 2 or as belonging to the Group 2 consisting of the Classes 1 and 3; . . . ; and the identifier $42_6$ identifies "the state of the driver" as belonging to the Group 1 consisting of the Class 2 or as belonging to the Group 2 consisting of the Class 3.

The inventors conducted an experiment to verify the effectiveness of the present invention using the state detecting device of the present invention and a driving simulator. Three male and female subjects (age of 21 to 23) were tested. One experiment cycle was 20 minutes. Each subject underwent ten experiment cycles. The driving simulator was configured to present a monotonous highway including random S-shaped curves.

In the experiment, in order to assess the accuracy, the assessment foil tula below was used, in which t is the number of experiment cycles (experiment number), T is the highest number of t, n is the number of samplings, $y_t$ is the accuracy label of t, and $H_t$ is the hypothesis of t (state estimate result). In the experiment, data were sampled every 10 seconds for 20 minutes; therefore, n is 120.

[Formula 6]

$$\text{Accuracy} = \frac{\sum_{t=1}^{T}\sum_{i=1}^{n}[y_t^i \in H_t(x_t^i)]}{nT}. \quad (6)$$

As seen from the table below, the experimental results revealed that the state detecting device of the present invention detects the driving state of a driver with an accuracy rate of 93.56%. This accuracy rate is 1.5 to 3 times higher than the other methods.

TABLE 1

| Method | Accuracy Rate [%] |
| --- | --- |
| LDA | 31.33 |
| k-NN | 33.75 |
| HD-ECOC | 58.28 |
| LD-ECOC | 93.56 |

<Embodiment 2>

Embodiment 2 of the present invention will be described hereafter with reference to FIGS. 6 and 7.

Here, the same or equivalent components as or to those of the state detecting device 10 according to Embodiment 1 are referred to by the same reference numbers and their explanation is omitted.

In the state detecting device 10 according to Embodiment 2, the identification device 30 is realized by a conventional computer.

Figure 6:
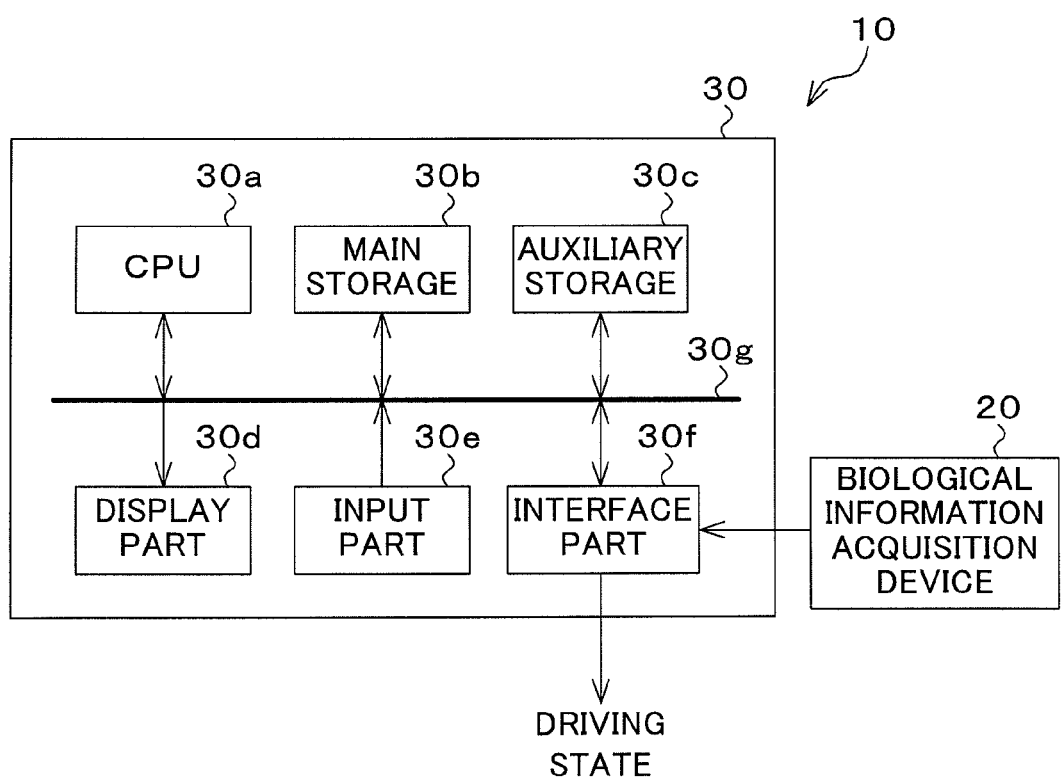
[FIG. 6] A block diagram of the state detecting device according to Embodiment 2.
Figure 7:
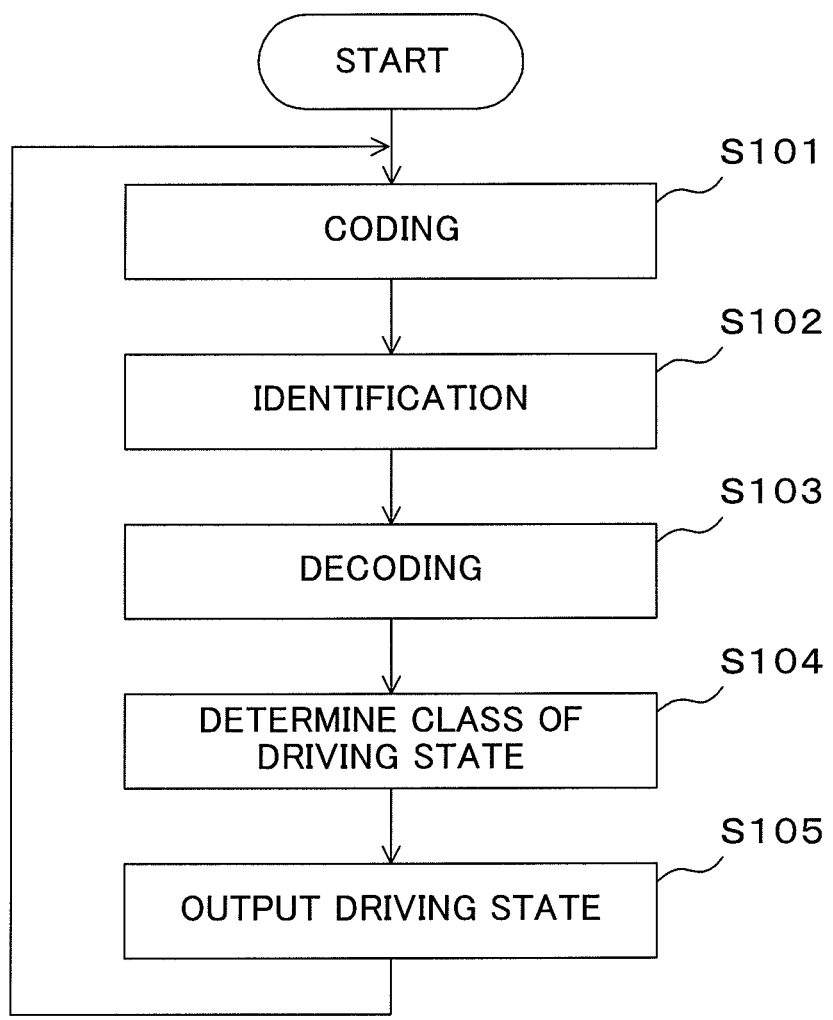
[FIG. 7] A flowchart for explaining the operation of the identification device.

The state detecting device 10 comprises, as shown in FIG. 6, a biological information acquisition device 20 and an identification device 30 realized by a computer.

The identification device 30 comprises a CPU (central processing unit) 30a, a main storage 30b, an auxiliary storage 30c, a display part 30d, an input part 30e, an interface part 30f, and a system bus 30g connecting the parts 30a to 30f to each other.

The CPU 30a executes a procedure described later on the input information x acquired by the biological information acquisition device 20 according to programs stored in the auxiliary storage 30c.

The main storage 30b is configured with a RAM (random access memory) and used as the work area of the CPU 30a.

The auxiliary storage 30c is configured with a nonvolatile memory such as a ROM (read only memory), magnetic disk, and semiconductor memory. The auxiliary storage 30c stores programs executed by the CPU 30a and various parameters. The auxiliary storage 30c further stores the input information x output from the biological information acquisition device 20 and information including results of processing by the CPU 30a.

The display part 30d is configured with a CRT (cathode ray tube) or LCD (liquid crystal display) and displays results of processing by the CPU 30a.

The input part 30e is configured with a keyboard and a pointing device such as a mouse. Instruction from the operator is entered through the input part 30e and informed to the CPU 30a via the system bus 30g.

The interface part 30f is configured with a serial interface or LAN (local area network) interface. The biological information acquisition device 20 is connected to the system bus 30g via the interface part 30f.

The procedure executed by the identification device 30 will be described hereafter with reference to FIG. 7. This procedure is executed after the CPU 30a instructs the biological information acquisition device 20 to acquire biological information and receives the input information x from the biological information acquisition device 20.

In the first step S101, the CPU 30a associates the code [1, −1, −1], code 2 [−1, 1, −1], code 3 [−1, −1, 1], code 4 [1, −1, 0], code 5[1, 0, −1], and code 6[0, 1, −1] each consisting of the three elements in the rows 1 to 6 of the code table W with the input information x, respectively.

In the next step S102, the CPU 30a divides the Classes 1 to 3 into the classes belonging to the Group 1 and the classes belonging to the Group 2 based on the codes 1 to 6. Then, the CPU 30a identifies the driving state of the driver as belonging to the Group 1 or as belonging to the Group 2 based on the input information x and calculates the identification values $h_1(x)$ to $h_6(x)$ corresponding to the identification results.

In the next step S103, the CPU 30a calculates the loss values $L_1$ to $L_3$ corresponding to the Classes 1 to 3, respectively, using the identification values $h_1(x)$ to $h_6(x)$ and the elements in the column direction of the code table W. As shown in FIG. 4, for example, when the identification values $h_1(x)$ to $h_6(x)$ are −2, −7, 0.5, −1, −9, and 12, the loss value $L_1$ corresponding to the Class 1 is calculated as presented by the formula (4) above.

In the next step S104, the CPU 30a detects the class corresponding to the lowest loss value among the calculated loss values $L_1$ to $L_3$. For example, when the loss values $L_1$ to $L_3$ are 7018, −161667, and 153546, respectively, the CPU 30a detects the Class 2 corresponding to the lowest loss value $L_2$ as the class to which the driving state of the driver belongs.

In the next step S105, the CPU 30a outputs information regarding the detected class to an external device. Then, the CPU 30a repeats the procedure from the step S101 to the step S105.

As described above, the state detecting device 10 according to this Embodiment 2 detects the class to which the current driving state of the driver belongs based on the driver's characteristic quantities represented by biological information such as the eyelid opening degree and frequency of heartbeat of the driver. The class is one of multiple classes defined by classifying the driving state of the driver using the activity level of the driver as an indicator. Therefore, to what degree the activity level of the driver is impaired can be detected by the level based on the detected class regardless of difference between individuals or difference in an individual. Consequently, driving assist more proper to the driver can be provided.

Embodiments of the present invention are described above. The present invention is not confined to the above embodiments.

For example, in the above embodiments, biological information is used as information regarding the driver. The present invention is not confined thereto. As information regarding the driver, for example, information regarding the vehicle such as the steering wheel angle, vehicle drifting degree, brake timing, and vehicle speed and acceleration, information regarding the circumstances around the driver such as the temperature and humidity in the vehicle, and information regarding equipment operation other than driving operation such as audio and air conditioner operation can be acquired. The state detecting device of the present invention can take such information into consideration to detect the class to which the driving state belongs.

Furthermore, the state detecting device 10 detects the state of a driver driving a vehicle. The present invention is not confined thereto. The state detecting device of the present invention is suitable for detecting the state of a driver or operator of a train or aircraft. Furthermore, besides the drivers, the state detecting device of the present invention can be used, for example, for detecting the depth of sleep of a monitored subject in a room.

Furthermore, the activity level of the driver can be determined, for example, based on an indicator fluctuating according to the degree of drowsiness and/or fatigue of a monitored subject. The activity level of the driver can be defined, for example, based on the accuracy of behavior or attentiveness of the driver (monitored subject).

Furthermore, the loss values can be calculated, for example, using a sigmoid function.

Furthermore, the function of the identification device 30 can be realized by dedicated hardware or by a conventional computer system.

The programs stored in the auxiliary storage 30c of the identification device 30 in Embodiment 2 can be stored and distributed on a computer-readable recording medium such as a flexible disk, CD-ROM (compact disk read-only memory), DVD (digital versatile disk), and MO (magneto-optical disk) and installed on a computer to configure a device executing the above-described procedure.

Furthermore, the programs can be stored on a disk device of a given server unit on a network such as the Internet. For example, the programs can be superimposed on carrier waves and downloaded on a computer.

Furthermore, the programs can be activated and executed while being transferred via a communication network.

Furthermore, it is possible to execute all or some of the programs on a server unit and transmit/receive information regarding the processing via a communication network for executing the above-described procedure.

When the above function is realized by an OS (operation system) in part or by cooperation of an OS and application programs, only the portion other than the OS can be stored and distributed on a medium or downloaded on a computer.

Various embodiments and modifications can be made to the present invention without departing from the broad spirit and scope of the present invention. The above-described embodiments are given for explaining the present invention and do not confine the present invention in any way.

Industrial Applicability

The state detecting device, state detecting method, and non-transitory computer-readable medium of the present invention is suitable for detecting the state of a monitored subject.

Description of Reference Numerals

| 10 | state detecting device |
| 20 | biological information acquisition device |
| 30 | identification device |
| 30a | CPU |

-continued

Description of Reference Numerals

| 30b | main storage |
| 30c | auxiliary storage |
| 30d | display part |
| 30e | input part |
| 30f | interface part |
| 30g | system bus |
| 40 | identification unit |
| 41 | coder |
| $42_1$ to $42_6$ | identifier |
| 43 | decoder |
| 1 | class detection unit |

The invention claimed is:

1. A state detecting device, comprising:
a characteristic quantity detector for detecting information regarding a monitored subject as characteristic quantities;
a sorter for sorting multiple classes defining the activity level of a monitored subject into a first group and a second group based on a code table, each group having at least one or more classes, and associating the sorted multiple classes with the characteristic quantities detected by the characteristic quantity detector;
multiple identification devices for receiving the characteristic quantities associated by the sorter as input values, identifying whether a state of the monitored subject belongs to the first group or the second group based on the input values, and outputting information including the identification results and credibility level as output values;
a loss value calculator for calculating loss values of the each class based on the each output values output from the multiple identification devices and the code table; and
a class detector for detecting a class to which the state of the monitored subject belongs among the multiple classes based on the loss values of the each class;
wherein the code table is determined by the number of identification devices and the number of classes.

2. The state detecting device according to claim 1, wherein:
said multiple classes are sorted into said first group and second group in multiple patterns.

3. The state detecting device according to claim 1, wherein:
said loss value calculator defines said loss values using an exponential function.

4. The state detecting device according to claim 1, wherein:
provided that the number of the classes is G, the number of the identification device is p and the code table is W,
the sorter sorts, among elements corresponding to each of the multiple classes which are arranged in the row direction of the code table presented by $W \in \{1, 0, -1\}^{p \cdot G}$, the classes corresponding to the elements of a value "1" into the first group, the classes corresponding to the elements of value "−1" into the second group and the classes corresponding to the elements of a value "0" into neither the first group nor the second group, and supplies the input values to the identification device corresponding to the row of the code table, the input values associating the characteristic quantity with the multiple classes which are sorted into the first group and the second group, each group having at least one or more classes;
wherein
the identification device identifies whether the state of the monitored subject belongs to the first group or the second group based on the input values supplied from the sorter, and outputs information including the identification results and credibility level as output values.

5. The state detecting device according to claim 4, wherein:
the loss value calculator calculates the loss values of each class corresponding to each column of the code table based on the each output value output for the each identification device from the multiple identification devices and elements arranged in the column direction of the code table.

6. The state detecting device according to claim 5, wherein:
the class detector detects the class in which the loss is the smallest among losses of the each class calculated by the loss value calculator as the class to which the state of the monitored subject belongs.

7. The state detecting device according to claim 1, wherein:
the information regarding said monitored subject is biological information of said monitored subject.

8. The state detecting device according to claim 7, wherein:
the biological information of said monitored subject includes at least one of information on the sight line of said monitored subject and information on the heartbeat of said monitored subject.

9. The state detecting device according to claim 1, wherein:
the characteristic quantity detector supplies the detected characteristic quantities to said identification device.

10. A state detecting method, comprising:
a characteristic quantity detecting process to detect information regarding a monitored subject as characteristic quantities;
a sorting process to sort multiple classes defining the activity level of a monitored subject into a first group and a second group based on a code table determined by the number of identification devices and the number of classes, each group having at least one or more classes, and associate the sorted multiple classes with the characteristic quantities detected in the characteristic quantity detecting process;
an identification process to receive the characteristic quantities that are associated in the sorting process as input values, identify whether the state of the monitored subject belongs to the first group or the second group based on the input values, and output information including the identification results and credibility level as output values;
a loss value calculation process to calculate loss values of the each class based on the output values output in the identification process and the code table; and
a class detection process to detect a class to which the state of the monitored subject belongs among the multiple classes based on the loss values of the each class.

11. A non-transitory computer-readable medium stored a program that allows a computer to execute the following steps:
a characteristic quantity detecting step for detecting information regarding a monitored subject as characteristic quantities;
a sorting step for sorting multiple classes defining the activity level of a monitored subject into a first group and a second group based on a code table determined by the number of identification devices and the number of classes, each group having at least one or more classes, and associating the sorted multiple classes with characteristic quantities detected in the characteristic quantity detecting step;
an identification step for receiving the characteristic quantities that are associated in the sorting step as input values, identifying whether the state of the monitored subject belongs to the first group or the second group based on the input values, and outputting information including the identification results and credibility level as output values;
a loss value calculation step calculating loss values of each class based on the output values output in the identification step and the code table; and
a class detection step for detecting a class to which the state of the monitored subject belongs among the multiple classes based on the loss values of the each class.

\* \* \* \* \*